(12) United States Patent
Joshi

(10) Patent No.: US 12,138,391 B1
(45) Date of Patent: Nov. 12, 2024

(54) INTUBATION APPARATUS

(71) Applicant: Shailendra Joshi, Ho Ho Kus, NJ (US)

(72) Inventor: Shailendra Joshi, Ho Ho Kus, NJ (US)

( * ) Notice: Subject to any disclaimer, the term of this patent is extended or adjusted under 35 U.S.C. 154(b) by 636 days.

(21) Appl. No.: 17/458,710

(22) Filed: Aug. 27, 2021

(51) Int. Cl.
*A61M 16/04* (2006.01)

(52) U.S. Cl.
CPC .... *A61M 16/0488* (2013.01); *A61M 16/0434* (2013.01)

(58) Field of Classification Search
CPC ...... A61M 25/0102; A61M 2025/0063; A61M 16/0488; A61M 16/0434–0459
See application file for complete search history.

(56) References Cited

U.S. PATENT DOCUMENTS

| | | | | |
|---|---|---|---|---|
| 4,388,076 A * | 6/1983 | Waters | ...................... | A61J 15/00 604/533 |
| 4,655,214 A * | 4/1987 | Linder | ............... | A61M 16/0488 128/207.14 |
| 9,526,856 B2 * | 12/2016 | Azagury | ............ | A61M 16/0434 |
| 2008/0066746 A1 * | 3/2008 | Nelson | ................... | A61M 16/04 128/200.26 |
| 2017/0246410 A1 * | 8/2017 | Levitan | ............. | A61M 16/0488 |
| 2020/0139081 A1 * | 5/2020 | Gardner | ................. | A61B 1/267 |
| 2020/0254229 A1 * | 8/2020 | Proxenos | .......... | A61M 25/1002 |

\* cited by examiner

*Primary Examiner* — Joseph D. Boecker
*Assistant Examiner* — Thomas W Greig
(74) *Attorney, Agent, or Firm* — Gulf Coast Intellectual Property Group

(57) ABSTRACT

An intubation apparatus configured to operably couple with an endotracheal tube so as to provide assistance in the insertion process of the endotracheal tube. The intubation apparatus of the present invention includes an elongated cylindrical body having an angular insertion tip on one end thereof. The body has an exterior surface wherein the first embodiment of the tube anchors is secured thereto. A second embodiment of a tube anchor is present within the scope of the invention and includes an air bladder integrally formed with the body wall. The two embodiments of the tube anchors function to apply a bias force against an inner wall of the endotracheal tube so as to maintain a position therewith. For the second embodiment of the tube anchor a syringe adapter is present that is configured to operably couple a syringe to the body and further provide a sealable connection with the endotracheal tube.

3 Claims, 3 Drawing Sheets

INTUBATION APPARATUS

FIELD OF THE INVENTION

The present invention relates generally to medical equipment, more specifically but not by way of limitation, an intubation apparatus that is utilized in conjunction with an endotracheal tube wherein the apparatus of the present invention is operably coupled with and conjunctively functions with an endotracheal tube so as to facilitate an improved intubation process of a patient.

BACKGROUND

A medical bougie is a thin elongated cylindrical shaped object that is typically manufactured from a suitable material such as rubber or plastic that is utilized by a physician or other healthcare provider. The user of the bougie inserts into or through a body passageway, such as the esophagus to diagnose or treat a condition. It is very common for a healthcare worker to utilize a bougie in combination with an endotracheal tube so as to perform an intubation on a patient. Alternatively, a bougie may be used to widen a passageway, guide another instrument into a passageway, or dislodge an object. Conventional bougies are typically long and slightly unwieldy wherein an average bougie is often sixty to seventy centimeters in length. The top of a conventional bougie is most often malleable and has an angle of approximately forty-five to sixty degrees. The outside diameter of a conventional bougies typically averages five to six millimeters.

There are many problems with the existing design of the bougie. In addition to the physical dimensions being unable to promote efficient handling, conventional bougies are not configured to hold a device such as but not limited to an endotracheal tube in place. The bougie is considered to be a bind instrument and a camera is necessary if a practitioner wishes to see a graphic image of the progress of the bougie or an area adjacent the tip thereof. Most often when performing an intubation utilizing a bougie an practitioner will require an assistant.

Accordingly, there is a need for an improved bougie that is configured to operate in conjunction with an endotracheal tube wherein the present invention is placed within the passage of an endotracheal tube and can anchor its position relative thereto.

SUMMARY OF THE INVENTION

It is the object of the present invention to provide a medical apparatus that is configured to be utilized in conjunction with an endotracheal tube wherein the present invention includes an elongated cylindrical body.

Another object of the present invention is to provide an apparatus operable to conjunctively function with an endotracheal tube so as to function therewith as a single assembly wherein the present invention includes an angled malleable tip.

A further object of the present invention is to provide a medical apparatus that is configured to be utilized in conjunction with an endotracheal tube wherein the body includes an exterior surface wherein the exterior surface of the body includes anchors extending outward therefrom.

Still another object of the present invention is to provide an apparatus operable to conjunctively function with an endotracheal tube so as to function therewith as a single assembly wherein the present invention further includes an endotracheal tube adapter.

An additional object of the present invention is to provide a medical apparatus that is configured to be utilized in conjunction with an endotracheal tube wherein the endotracheal tube adapter secures the endotracheal tube in a manner so as to facilitate rotation thereof so as to adjust the tip angle thereto.

Yet a further object of the present invention is to provide an apparatus operable to conjunctively function with an endotracheal tube wherein during use of the present invention the user engages the endotracheal tube.

Another object of the present invention is to provide a medical apparatus that is configured to be utilized in conjunction with an endotracheal tube wherein the anchors on the body of the present invention include a first embodiment and a second embodiment.

An alternative object of the present invention is to provide an apparatus operable to conjunctively function with an endotracheal tube wherein the endotracheal tube includes a syringe adapter formed on the top surface thereof.

Yet a further object of the present invention is to provide a medical apparatus that is configured to be utilized in conjunction with an endotracheal tube wherein the syringe adapter includes a port operable to be moved between an open position and a closed position.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
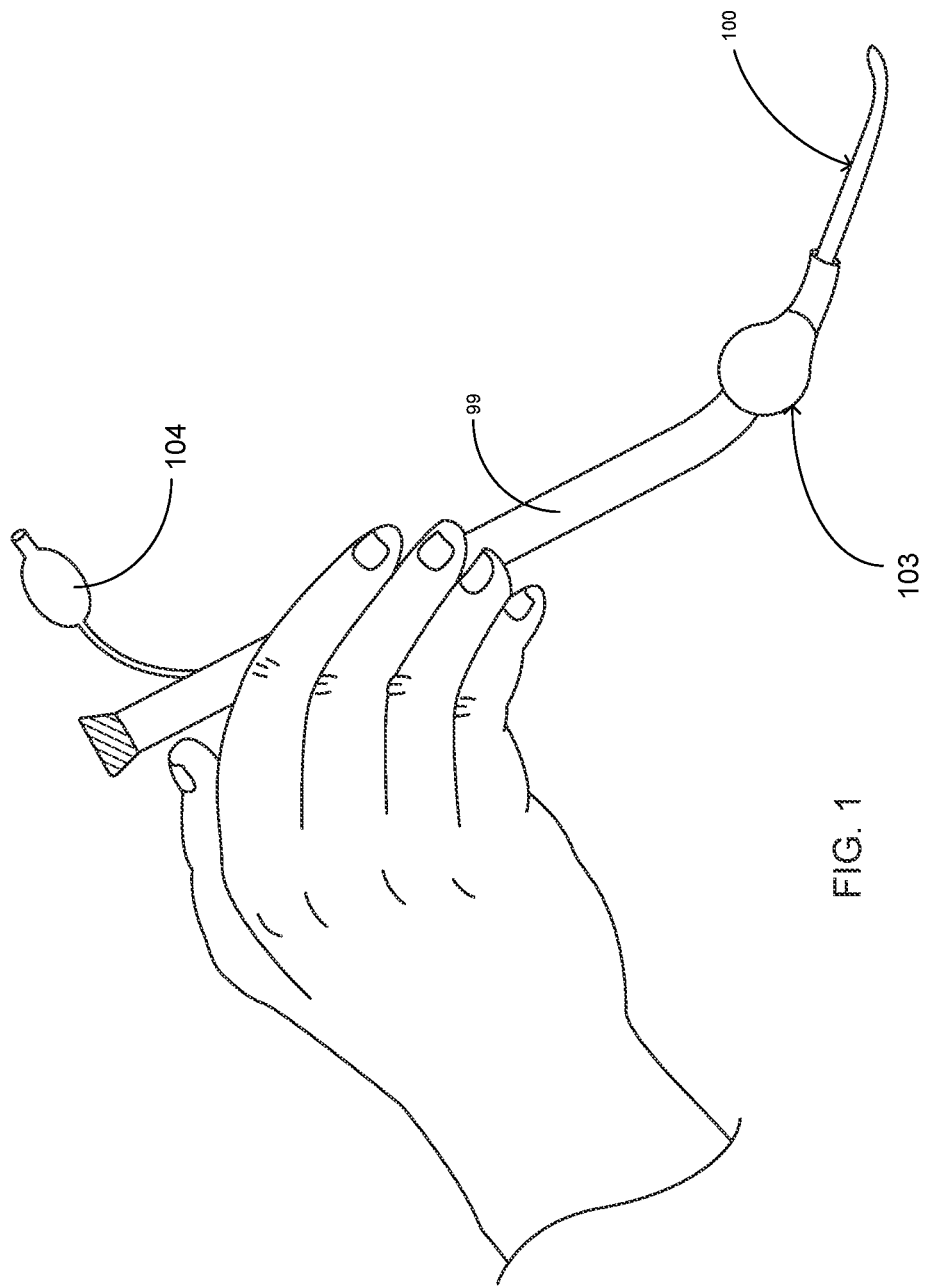
FIG. 1 is a perspective view of the present invention engaged with an endotracheal tube.

Referring now to the drawings submitted herewith, wherein various elements depicted therein are not necessarily drawn to scale and wherein through the views and figures like elements are referenced with identical reference numerals, there is illustrated an intubation apparatus 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

Referring in particular to the Figures submitted as a part hereof, the intubation apparatus 100 includes a body 10 wherein the body 10 is elongated in manner and being manufactured from a flexible material such as but not limited to rubber or plastic. The body 10 includes a first end 11 and second end 12 wherein a hollow passage 14 extends intermediate thereto. While no particular length of the body 10 is required, it is contemplated within the scope of the present invention that the body 10 is provided in a length between forty five and seventy centimeters. The second end 12 includes insertion tip 15 that is integrally formed with body 10. The insertion tip 15 is angularly oriented with the body 10 wherein the insertion tip 15 is approximately forty-five degrees with respect to the body 10. The insertion tip 15 can be configured so as to have integrally formed therewith a LED light and a camera that are operably connected to a remote monitor so as to provide visual data to the user of the intubation apparatus 100.

The intubation apparatus 100 is configured to be operably coupled with a conventional endotracheal tube 99. As is known in the art, the endotracheal tube 99 is utilized to provide intubation of a patient. Conventional endotracheal tube 99 are configured with inflatable cuff 103 that is operably coupled to inflation balloon 104. The endotracheal tube 99 includes a first end 98, second end 97 and a hollow passage 96 extending therethrough. The intubation apparatus 100 as will be further discussed herein is configured to be inserted into the hollow passage 96 of the endotracheal tube 99 and partially extend outward from second end 97 so as to provide guidance and positioning of the endotracheal tube 99. In order to effectively maintain a desired position between the endotracheal tube 99 and the body 10 of the intubation apparatus 100, the exterior surface 7 of the body 10 includes tube anchors 25, 30 formed thereon. The tube anchors 25, 30 are provided in a first embodiment and a second embodiment and function to bias against the inner wall surface 95 of the endotracheal tube 99 so as to maintain a position between the body 10 and the endotracheal tube 99.

Figure 2:
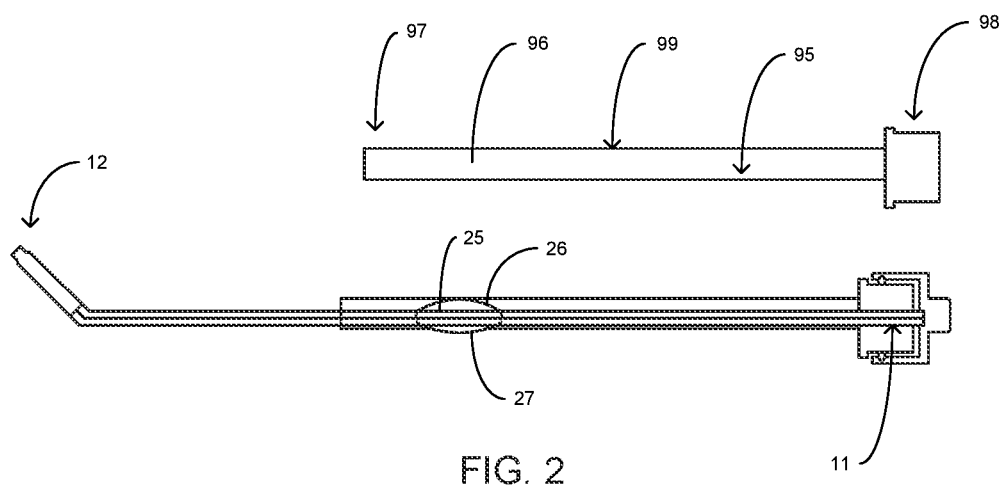
FIG. 2 is a side diagrammatic view of the present invention engaged with an endotracheal tube and an endotracheal tube showing anchors in first position.
Figure 3:
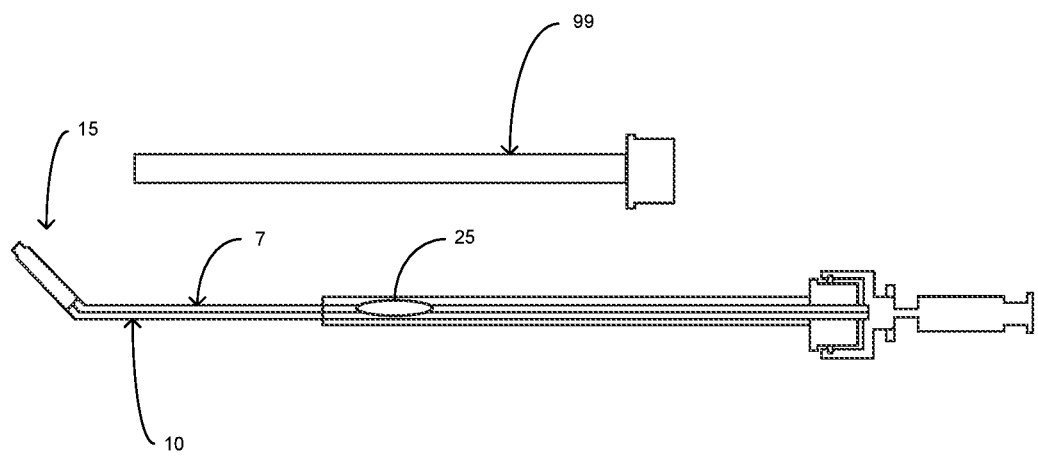
FIG. 3 is a side diagrammatic view of the present invention engaged with an endotracheal tube and an endotracheal tube showing anchors in second position.

The first embodiment of the tube anchor 25 are illustrated in FIGS. 2 and 3 herein. The tube anchor 25 is comprised of a first member 26 and a second member 27 that are diametrically opposite on the exterior surface 7 of the body 10. The first member 26 and second member 27 are secured to the exterior surface 7 utilizing suitable durable techniques. The first member 26 and second member 27 are manufactured from a resilient material such as but not limited to plastic and are planar in manner. First member 26 and second member 27 are arcuate in shape and are operable to be moved between a first position and a second position. In the first position the first member 26 and second member 27 extend outward from the exterior surface 7 of the body 10. Subsequent being inserted into an endotracheal tube 99, the first member 26 and second member 27 of the tube anchor 25 compress inwards towards the body 10 and provide a bias force against the inner wall surface 95 of the endotracheal tube 99. Ensuing the compression of the first member 26 and second member 27 of the tube anchor 25, the tube anchor 25 is in its second position wherein the tube anchor 25 functions to assist in maintaining a desired position between the body 10 of the intubation apparatus 100 and the endotracheal tube 99. The aforementioned improves the ability for a user to properly position the endotracheal tube 99 within a patient. It is contemplated within the scope of the present invention that the first member 26 and second member 27 of the tube anchor 25 could be provided in alternate lengths and radius so as to provide the desired function as discussed herein. Furthermore, it is contemplated within the scope of the present invention that the first member 26 and second member 27 could have only one end thereof secured to the exterior surface 7 of the body 10 with the opposing end adjacent to the exterior surface 7 but not secured thereto in order to provide an alternate structure of facilitating movement of the tube anchor 25 intermediate its first position and second position. While a first member 26 and second member 27 are illustrated and discussed herein comprising the tube anchor 25, it is contemplated within the scope of the present invention that the tube anchor 25 could employ only one member formed as described herein for the first member 26 and second member 27 and achieve the desired function discussed herein.

Figure 4:
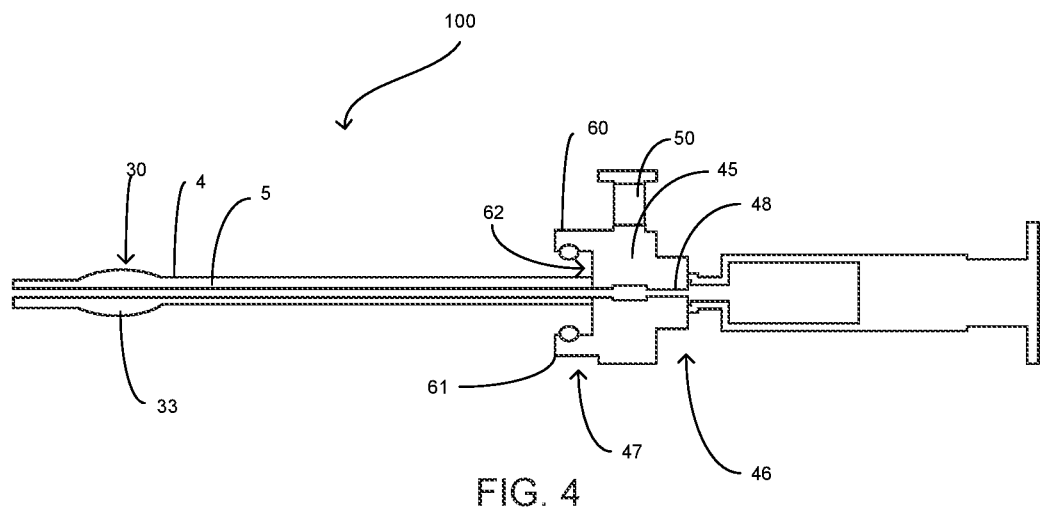
FIG. 4 is a side diagrammatic view of the present invention having a second embodiment of an anchor.
Figure 5:
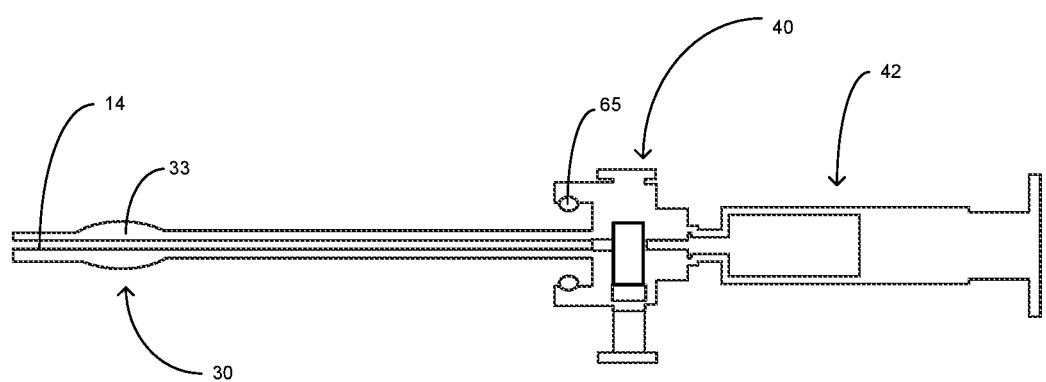
FIG. 5 is a side diagrammatic view of the present invention having a second embodiment of an anchor with the syringe port in a closed position.

Referring now to FIGS. 4 and 5 submitted herewith, the second embodiment of the tube anchor 30 is illustrated therein. The tube anchor 30 includes an inflatable bladder 33 that is integrally formed in the exterior surface 7 of the body 10. The inflatable bladder 33 is operably coupled to syringe adapter 40 through hollow passages 5 in the body wall 4 so as to facilitate inflation thereof utilizing a syringe 42. The tube anchor 30 is transitioned intermediate a first position and a second position through introduction of air into the bladder 33. In the first position the bladder 33 is deflated so as to facilitate insertion of the body 10 of the intubation apparatus 100 into the endotracheal tube. Subsequent inflation of the bladder 33, the tube anchor 30 extends outward from the exterior surface 7 of the body 10 so as to bias against the inner wall surface 95 of the endotracheal tube 99. In this second position the body 10 is fixedly positioned with respect to the endotracheal tube 99.

Syringe adapter 40 is operably coupled to the body 10 utilizing suitable techniques. The syringe adapter 40 include a body member 45 being manufactured from a suitable material such as but not limited to plastic. Body member 45 includes first end 46 and second end 47. A passage 48 extends through body member 45 wherein the passage 48 facilitates the introduction of air from the syringe 42 so as to provide inflation of the bladder 33. The passage 48 is moved between an open and closed position utilizing rod 50 wherein the rod 50 is moved in an upward-downwards movement in order to provide opening and closing of the passage 48. It is contemplated within the scope of the present invention that the passage 48 could be opened and closed utilizing alternate elements such as but not limited to valves.

Contiguously formed with the body member 45 proximate second end 47 are tube engagement members 60,61. The tube engagement members 60,61 extend outward from second end 47 and form a void 62 therebetween. Void 62 is of suitable size so as to accommodate the first end 98 of the endotracheal tube 99 therein. Secured to the tube engagement members 60,61 is an O-ring 65 wherein the O-ring 65 is operable to sealably secure the second end 98 within the void 62. While the tube engagement members 60,61 secure the end 98 of the endotracheal tube 99, the endotracheal tube 99 is still rotatably movable with respect to the intubation apparatus 100 in order to provide alteration of the angle of the insertion tip 15 relative to the endotracheal tube 99 as needed for proper insertion of the endotracheal tube 99. While not particularly illustrated herein, it is contemplated within the scope of the present invention that the body member 45 could have therein connectors such as but not limited to USB connectors so as to facilitate operable connection with a camera located on the insertion tip 15 and a remote computing device.

It should be understood that while FIGS. 2 and 3 submitted herewith illustrate the syringe adapter 40 and syringe 42, that in the first embodiment of the tube anchor 25 the aforementioned elements are not utilized to provide operation of the intubation apparatus 100 having the tube anchor 25. Furthermore, it is contemplated within the scope of the present invention that the body 10 could be provided having both the first embodiment and second embodiment of the tube anchors 25,30 in order to provide the ability for a user to select utilization of one or the other based on preference.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. An apparatus configured to operably couple with an endotracheal tube so as to assist in an intubation procedure of a patient wherein the apparatus comprises:
    a body, said body being elongated and cylindrical in shape, said body having a first end and a second end, said body having a wall, said wall of said body having a passage therethrough, said second end of said body having an insertion tip, said insertion tip being angular with respect to said body;
    a tube anchor, said tube anchor integrally formed with said wall of said body, said tube anchor having a bladder, said bladder being operably coupled to said passage present in said wall of said body, said bladder having a first position and a second position, said bladder having an interior volume, wherein in said first position said interior volume of said bladder is substantially empty and wherein in said second position said interior volume of said bladder has compressed air therein so as to extend said tube anchor outward from said body;
    a syringe adapter, said syringe adapter being secured to said first end of said body, wherein the syringe adapter includes a body member, said body member of said syringe adapter having a first end and a second end, said body member having tube engagement members extending outward from said second end of said body member, wherein said tube engagement members have a void therebetween configured to receive an end of the endotracheal tube, said tube engagement members further having a sealing member so as to sealably secure the endotracheal tube;
    wherein said tube anchor is operable to releasably secure said body within a hollow passage of the endotracheal tube.

2. The apparatus configured to operably couple with an endotracheal tube so as to assist in an intubation procedure of a patient as recited in claim 1, wherein said body member of said syringe adapter further includes a passage extending therethrough.

3. The apparatus configured to operably couple with an endotracheal tube so as to assist in an intubation procedure of a patient as recited in claim 2, wherein said passage within said body member of said syringe adapter can be transitioned between an open position and a closed position.

* * * * *